United States Patent [19]

Benecke et al.

[11] Patent Number: 5,454,472

[45] Date of Patent: Oct. 3, 1995

[54] METHOD OF CONTINUOUSLY SEPARATING MIXTURES OF MICROSCOPIC DIELECTRIC PARTICLES AND APPARATUS FOR CARRYING THROUGH THIS METHOD

[75] Inventors: Wolfgang Benecke; Bernd Wagner; Rolf Hagedorn; Günter Fuhr; Torsten Müller, all of Berlin, Germany

[73] Assignee: Fraunhofer Gesellschaft zur Forderung der angewandten Forschung e.V., Munich, Germany

[21] Appl. No.: 196,093

[22] PCT Filed: Aug. 19, 1992

[86] PCT No.: PCT/DE92/00694

§ 371 Date: Feb. 18, 1994

§ 102(e) Date: Feb. 18, 1994

[87] PCT Pub. No.: WO93/03850

PCT Pub. Date: Mar. 4, 1993

[30] Foreign Application Priority Data

Aug. 19, 1991 [DE] Germany ............... 41 27 405.9

[51] Int. Cl.[6] .................................................. B03C 1/30
[52] U.S. Cl. .................. 209/127.1; 209/128; 209/212
[58] Field of Search ................... 209/128, 129, 209/130, 127.1, 636, 212, 213, 214, 576, 638

[56] References Cited

U.S. PATENT DOCUMENTS

| | | | |
|---|---|---|---|
| 4,172,028 | 10/1979 | Dunn | 209/127.1 |
| 4,517,078 | 5/1985 | Inculet et al. | 209/128 |
| 4,627,579 | 12/1986 | Rich | 209/129 |
| 4,680,106 | 7/1987 | Weiss et al. | 209/127.1 |
| 4,816,143 | 3/1989 | Vollmar | 209/212 |
| 5,224,604 | 7/1994 | Duczmal et al. | 209/128 |

*Primary Examiner*—Andres Kashnikow
*Assistant Examiner*—Lisa Douglas
*Attorney, Agent, or Firm*—Antonelli, Terry, Stout & Kraus

[57] ABSTRACT

A method of separating mixtures of microscopic dielectric particles in suspensions in an apparatus for carrying the method. A mixture of particles is forced onto guide paths by dielectrophoretic forces or by a flow of the suspension medium with an additional force, which is provided to compensate the force causing the particles to move along the guide paths for specific particle species causing the specific particle species to be fed out from the mixture of particles. The apparatus may be integrated on surfaces of silicon wafers at low cost and in mass-production numbers, and is suitable for isolating minute particles such as biological cells, cell organelles, bio molecules as well as organic dielectric particles.

23 Claims, 5 Drawing Sheets

METHOD OF CONTINUOUSLY SEPARATING MIXTURES OF MICROSCOPIC DIELECTRIC PARTICLES AND APPARATUS FOR CARRYING THROUGH THIS METHOD

DESCRIPTION

1. Field of the invention

The present invention relates to a method of continuously separating mixtures of microscopic dielectric particles, wherein the mixture of particles is suspended in a liquid or a gel, as well as to an apparatus for carrying through this method.

2. Prior Art

A separating method of this type is intended for isolating mixtures of microscopic particles such as biological cells, cell organelles, bio molecules as well as inorganic dielectric particles, and for preparing them for analyses or technological applications.

The isolation of certain species of particles from mixtures of particles is required, for instance, in medicine, in food engineering, biology, chemistry and for pharmaceutical purposes. Specifically when major quantities of a mixture are to be separated it is desirable to apply a continuously operating separating method.

Various electrokinetic methods have become known for separating mixtures of particles. Separating methods such as gel electrophoresis, iso-tachophoresis and iso-electric focussing are employed to separate mixtures of particles into their constituents by the latter's different mobilities. One decisive requirement for such a separation consists in the aspect that appropriate provisions reduce the convections, which occur in any case, down to a non-critical value since convection takes an influence on the mobility of the particles.

The reduction of convection is achieved either by cooling or by the application of convection-inhibiting carriers. There are defined limits if comparatively large-size particles such as biologic cells are to be separated or if the system is to be operated continuously. For this reason a continuous operation can be achieved only by expensive cooling provisions or by complex stabilizing techniques, e.g. with utilization of centrifugal forces.

The costs incurred thereby and the technological problems involved have resulted so far only in a restricted scope of application of continuously operating electrophoretic methods.

SUMMARY OF THE INVENTION

The present invention is based on the object of providing a method of separating mixtures of microscopic suspended particles, which operates continously, presents a high grade of separation, and which can be realized at low cost, as well as on the problem of providing an apparatus for carrying through the method.

This problem is solved, in accordance with the present invention, by a method That is, there is provided a method and apparatus for continuously separating mixtures of microscopic dielectric particles suspended in a liquid or a gel by one of (a) continuously forcing the particles to move on guide paths by applying high-frequency alternating fields as a guiding field, which present maxima and minima at microscopic spacings, and feeding certain particle species out from the guide path by applying at least one additional field of forces acting upon the particles and having a component orthogonal to the guide path and with compensation of the forces in forcing the motion of the certain particle species on the guide paths, and (b) forcing the particles onto guide paths by causing a suspension medium to flow in a presettable direction, and feeding certain particles species out from the flow by applying at least one dielectrophoretic high-frequency field acting upon the particles, with compensation force acting upon the particles as a result of the flow.

According to a feature of the present invention, the additional field of forces has a form of one of an electric field, a magnetic field, an optical field, a gravitational field, a field of flow, and a corpuscular flux.

The suspended particles are forced to move along a guide orbit or path, in one case by fields of dielectrophoretic force, and in the other case by the flow of the suspension medium.

An additional force compensates the forces which enforce a particle movement onto the guide paths for certain species of particles so that these particles are fed out from the guide paths and hence separated from the mixture.

In the first case, homogeneous fields of forces may be employed to this end, which present a sufficiently strong component orthogonal to the guide path, while in the second case the additional forces are induced by inhomogeneous alternating fields.

According to the present invention, the additional field of forces, which compensates the guiding forces may be an electric, a magnetic, an optic or a gravitational field. An electric field generated between two parallel electrodes by the application of a voltage, with the guided particles moving between the electrodes, is particularly simple to realize. The force may, however, also be exerted also by a field of flow, e.g. a flowing liquid moving with a component orthogonal to the guided particles, or by a corpuscular flux.

In accordance with a feature of the present invention the guiding field is a high-frequency field which travels in presettable directions. The frequency of the guiding field is determined by the dielectric properties of the particles to be separated; in the case of biologic particles it ranges typically at a few 100 kHz whilst the amplitude ranges at 5 V to 40 V. The travelling high-frequency field exerts forces of repulsion or attraction, respectively, on the suspended particles, which forces are caused by the interfacial charges, which are induced in the particles by the electric field, staying behind the travelling field vector. The motion of the particles is definitely non-synchronous relative to the electric field. The realization of such a travelling field is described exhaustively in the unpublished Gem Patent Application DE P 40 34 697.8.

A separating method is particularly flexible which generates a guiding field by means of a plurality of alternating fields which are different from each other in terms of frequency and phase. With this provision it is possible to ensure a highly variable formation of the force acting upon the guided particles.

In accordance with a feature of the present invention, the feedout of certain species of particles may be set by a variation of the additional field of forces, or by varying the force exerted upon the particles by the guiding field, depending on the desired selection.

In the apparatus for carrying through the method, the guiding field, a high-frequency field travelling in a presettable direction, is generated by at least one row of electrodes which, seen in the direction of the travelling field, are disposed in parallel relationship on a base body. The extension of the electrodes in the direction of the travelling field, as well as the inter-electrode spaces correspond approximately to the size of the particles in the mixture and typically ranges at a few μm in the case of biologic cells. The motion of the particles takes place above the electrodes. It is also possible, however, to dispose two rows of electrodes in such a way that they enclose an electrode-free channel therebetween. In that case the particles my be caused to move in the channel. The travelling field is generated by applying to the electrodes high-frequency voltages in an appropriate sequence by means of an electronic circuit.

In accordance with a feature of the present invention the electrodes are arranged either in one or in several lines, so as to constitute a linear passage for the particles. It is also possible to dispose the electrodes along curved paths so that also curved passages can be realized. The electrodes can be arranged for achieving selectively either a constant channel width or a channel width varying along the direction of the channel. The different arrangements allow for a highly flexible configuration of the passages.

A particularly expedient configuration of the invention includes a flow chamber which presents an inlet and an outlet opening. Two rows of electrodes enclose a passage which interconnects the two openings. An electric high-frequency travelling field is established by means of the rows of electrodes. The additional force for separating the mixture of particles is generated by the application of a voltage to two additional electrodes which are arranged in parallel relationship along the channel and produce the effect of a capacitor.

In order to prevent the particles deflected from the corpuscular flux from contacting these electrodes diaphragms are mounted between the electrodes and the rows of electrodes, which fill the entire cross-sectional area of the chamber. If particles are deflected from the mixture in one direction only a single diaphragm is sufficient.

The apparatus of the present invention allows for a splitting the flux of a mixture of particles into various sub-fluxes of different species of particles. To this end the passage formed by the rows of electrodes and by isolating layers is provided with a branch. In the channel section ahead of the branch the particles are spatially separated by means of additional electrodes and guided by the travelling field into the different channel branches. This apparatus is particularly well suited for a cascade arrangement by means of which a particularly efficient separation of the various species of particles is achieved.

In the apparatus of the present invention the flowing suspension medium forces the suspended mixture of particles onto a guide path. Along the guide channel electrode systems are arranged which serve to generate inhomogenous alternating electric fields in the flow channel. As a result of the field inhomogeneities the particles are subjected to dielectrophoretic forces which feed out certain species of particles from the mixture, depending on the flow rate and the field intensity.

In accordance with a feature of the present invention, the inhomogeneous fields are generated by means of two electrodes arranged in parallel relationship, which enclose the flow channel and present mutually facing surfaces which have relief-like surface irregularities such as crests and troughs. The fed-out particle species is selected via the frequency or intensity of the high-frequency alternating voltage applied between the plates. For preventing the fed-out particles from collecting on the electrodes it is expedient to provide the electrode material with through holes or a porous structure.

In accordance with a feature of the present invention, the inhomogenous fields are generated by means of two rows of electrodes in parallel relationship, which enclose the flow channel. The field inhomogeneities are achieved by different inter-electrode spaces in a row and by the application of a series of alternating voltages between adjacent electrodes, which are different, in terms of their intensity and frequency, from the voltages applied between adjacent electrodes of the other row.

In an improvement of the invention different electrode systems are applied on two sides of a thin flexible material. The flexible material is folded or wrapped in a way that a three-dimensional structure is formed which creates flow channels enclosed by electrode systems.

Another embodiment of such an apparatus is characterized by an elongate sheet with rows of electrodes applied on its two sides in mutual orthogonal relationship is wrapped to fore a reel. Isolating ribs applied on the electrodes one side of the sheet in the direction of the reel axis serve as spacers between the wrapped layers so that the suspension may flow through the reel along the latter's axis in the figure. The feed-out of the selected particle species from the mixture is achieved by the appropriate application of a high-frequency alternating voltage to the rows of electrodes on both sides.

In order to prevent the particles fed out from the mixture from interfering with the flux or depositing on the electrodes, elements defining the particle orbit which present traversable through holes or which are made of a porous material. The fed-out particles may escape through the orifices from the flow channel. Such orifices can be achieved in a particularly simple manner by the provision that an ultra-thin diaphragm is used as base body of the apparatus, having through holes etched therethrough.

In an apparatus according to a feature of the present invention, the electrode surfaces present relief-like structures, preferably longitudinal channels extending in the flow direction of the suspension medium. With this provision a lateral deflection of the flowing particles is avoided which are not fed out, so that the flux is smoothed. This smoothing of the flux results in an improvement of the grade of separation.

An improvement of the invention serves to take an influence on the travelling properties of the flowing particles. The insulating layer on the electrodes, which presents locally different thicknesses, causes the electric field to act upon the particles with locally different intensities. With this provision it is possible to manipulate the corpuscular flux efficiently since different preferred orbits can be created for the particles at different locations in the apparatus. The trough-shaped and corrugated structure of the coating serves to smooth and flexibly guide the corpuscular flux.

An inventive apparatus is preferably made of materials which are used in micro-structure technology and in micro-electronics, and it is produced with application of the techniques and processes common in these fields. The base body onto which the electrodes are applied is preferably made of silicon while the electrodes consist of gold.

The separating apparatus, together with an electronic circuit for controlling the electrodes and for an analysis of the motion of the particles, is integrated on a common base body, preferably a silicon wafer.

The inventive apparatus is well suitable for a cascade system. A tandem arrangement of several separating apparatuses produces a substantial improvement of the grade of separation. Good results can be obtained if a fed-out sub-flux is recycled to the initial apparatus and is recycled through the cascade. In many cases a very high grade of separation is achieved already if a fed-out sub-flux is recycled by one or two separating stages.

The advantages achieved by the present invention particularly reside in the aspect that, as contrasted with conventional separating methods, the proposed separation of the mixture presents a threshold character. Hence the separation only depends on whether a certain species of particle can or cannot leave its orbit. The threshold which determines the separation may be flexibly selected on account of the relationship between the dielectric guiding forces and the deflecting components, which is easy to influence. As a result it is easy to determine the particle species to be fed out while at the same time a high grade of separation is achieved.

The orbits set by the electrophoretic forces my be selected to be located freely in space so that high-performance flux systems can be designed for particle separation while carrier materials are dispensed with.

On account of the uncomplex structure of the apparatus and its suitability for system integration a low-cost separating apparatus is made available.

BRIEF DESCRIPTION OF THE DRAWINGS

The drawings are schematic illustrations of embodiments of the invention which will be described in the following in more details, without any restriction of the general inventive idea. In the drawing.

DESCRIPTION OF AN EMBODIMENT

Figure 1:
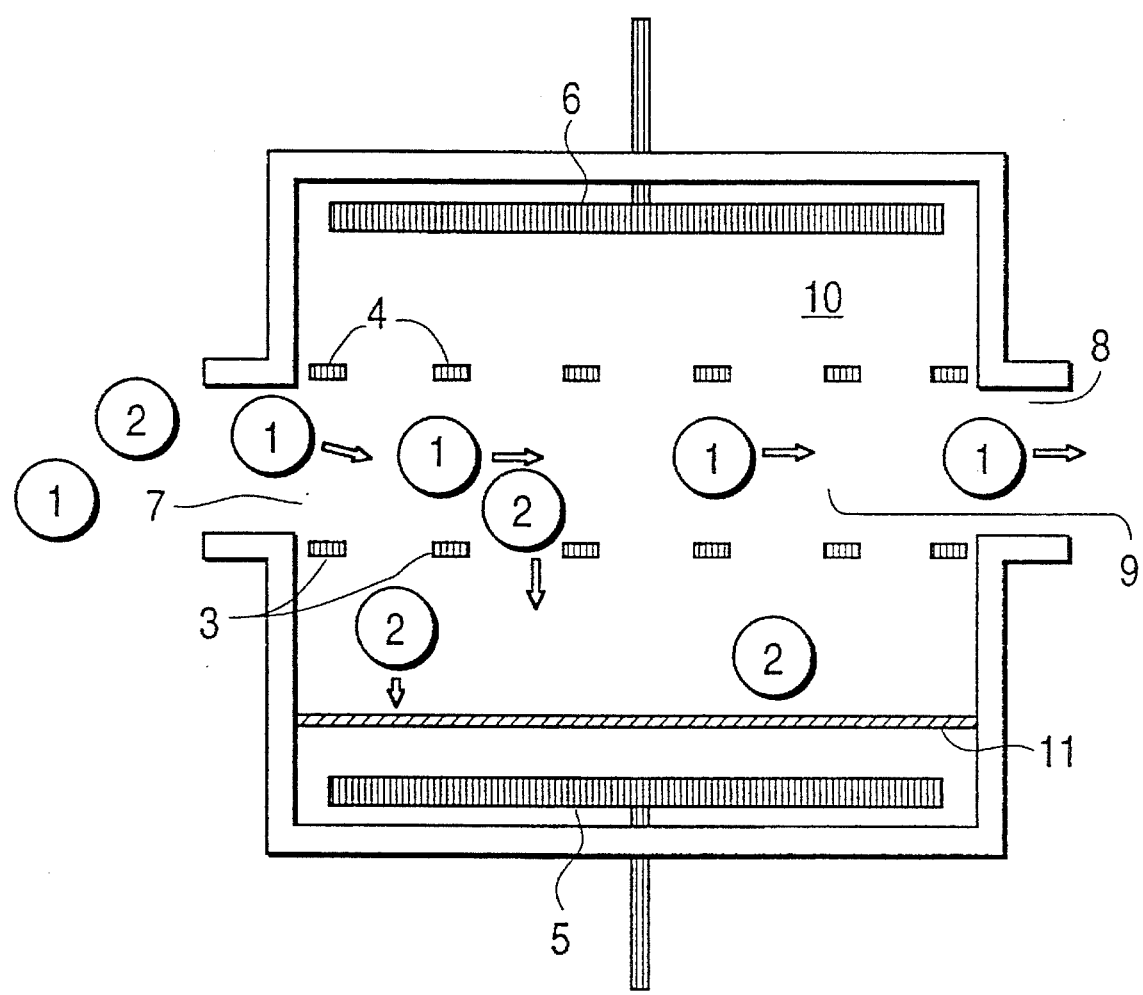
FIG. 1 illustrates an apparatus for continuous electrophoresis.

FIG. 1 shows an apparatus for continuously feeding out a species of particles from the flux of a suspended mixture of particles. A chamber 10 is provided with an inflow opening 7 and an outflow opening 8 for a flux of suspended particles 1, 2. Two rows of electrodes 3, 4 enclose a flow channel or passage 9 which interconnects the two openings 7, 8. The application of appropriate high-frequency alternating voltages to the electrodes 3, 4 causes the particles in the passage 9 to move through the chamber 10. The electrodes 5, 6, which are disposed in parallel with the passage 9, generate a field producing an electrophoretic effect.

If, for instance, the particle species 2 presents stronger superficial charges than the particle species 1 the field intensities may be selected so as to deflect only the particle species 2 from its guide path. The particle species 1 leaves the chamber 10 through the outflow opening 8. The diaphragm 11 prevents the fed-out particles 2 from contacting the electrode 5.

The techniques and processes of micro-structure technology my be employed to produce the apparatus on a non-illustrated substrate. The extension of the chamber 10 as well as of the electrodes 3 to 6 in a direction normal to the drawing plane, which is achieved by galvanic moulding, may amount up to a few 100 μm.

Figure 2:
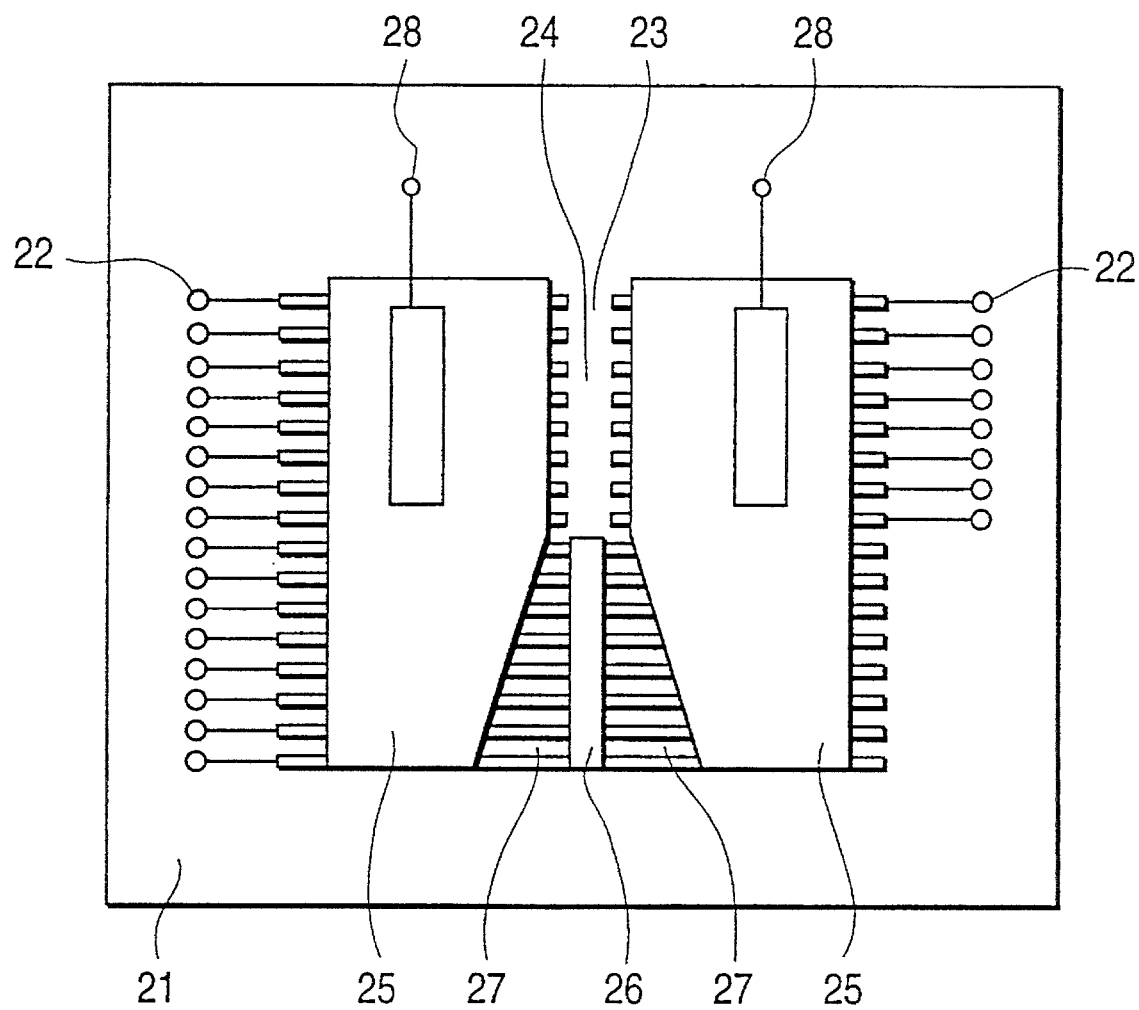
FIG. 2 shows a planar separation section.

FIG. 2 shows an apparatus for splitting a flux of a suspended mixture of particles into fluxes of different particle species. Sixteen planar electrodes 22 are applied on a base body 21. These electrodes are used to generate a travelling high-frequency field which moves the flux of the suspended mixture of particles in a direction orthogonal to the electrodes 22.

The first eight of the electrodes 22 present a central gap 23 so as to form a channel 24 extending in the direction of the travelling field. Two isolating layers 25, which enclose the channel 24 in the region of the first eight electrodes 22 and which are applied on the electrodes 22, shift this channel 24 in a direction towards the travelling field in such a manner that it presents an increasing channel width in the region of the continuous electrodes 22. In this region an additional isolating layer 26 is applied in the center of the channel, which bifurcates the widening channel 24 into two branch channels 27.

The two electrodes 28 which are applied onto the isolating layers 25 serve to generate an electrophoretically operative field which produces a spatial separation of different species of particles in the channel 24. The travelling field conveys the separated particles species into the various branch channels.

Figure 3:
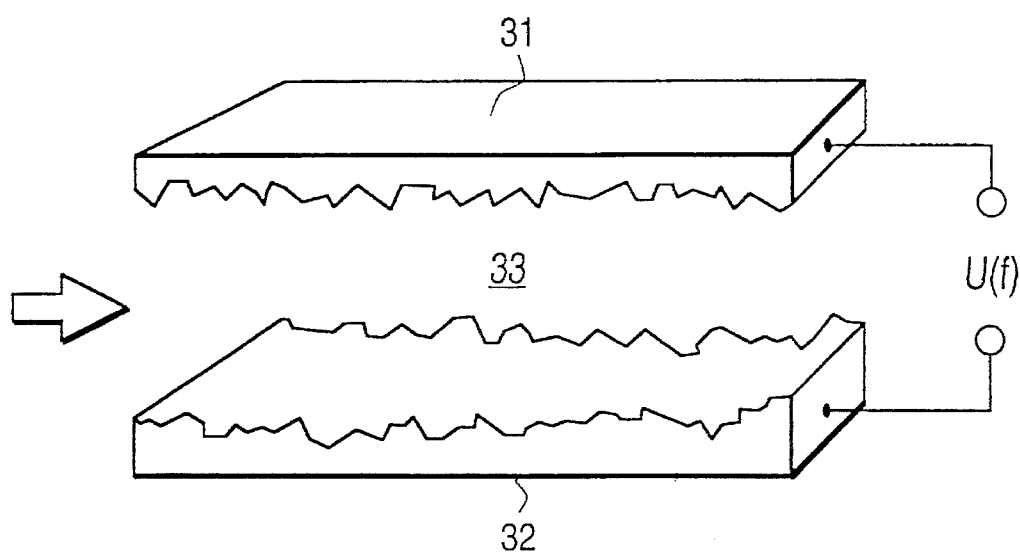
FIG. 3 shows a pair of electrodes for particle feed-out from the flux of a suspended mixture of particles.

FIG. 3 shows a pair of electrodes which is used to feed out particles from the flux of a suspended mixture of particles. The electrodes 31 and 32 enclose a flow channel 33. The arriving corpuscular flux is indicated by an arrow. The mixture of particles is moved through the apparatus by the flow of the suspension medium. Dielectrophoretic forces feed out particle of a certain species from the mixture in the channel 33. The field inhomogeneities which are required to this end are created by the surface irregularities of the electrodes 31, 32. The particle species to be fed out is selected by the selection of the frequency and intensity of the high-frequency alternating voltage U (f) applied between the electrodes 31, 32. The surfaces of the electrodes 31, 32 are structured in an etching process.

Figure 4:
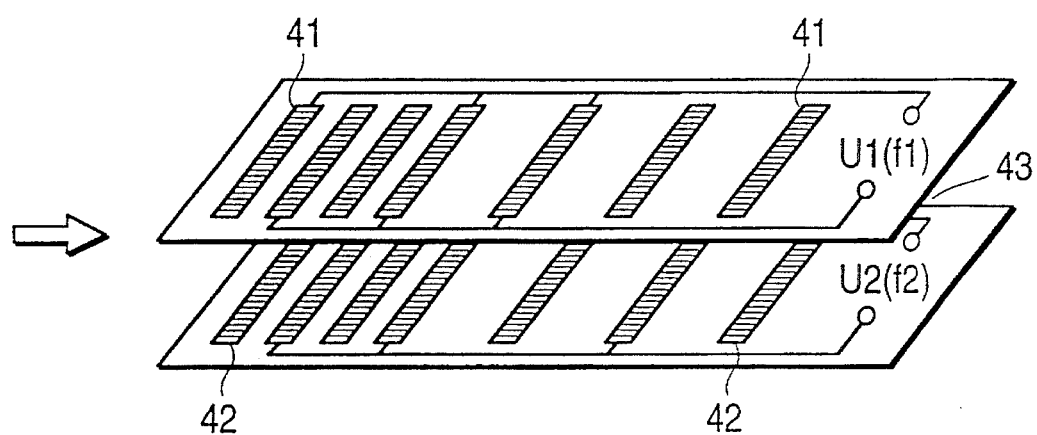
FIG. 4 shows an array of electrodes for particle feed-out from the flux of a suspended mixture of particles.

FIG. 4 illustrates an electrode array for feeding out particles from the flux of a suspended mixture of particles. Two rows of electrodes 41, 42 enclose a flow channel 43 through which passes the suspended corpuscular mixture indicated by an arrow. The elongate electrodes 41, 42 of the two rows are disposed in parallel relationship at non-uniform spacings. Respectively adjacent electrodes in a row are connected to different poles of a high-frequency voltage source. The dielectric holding forces, which are generated by means of the electrodes 41, 42, feed out different particle species from the corpuscular flux, with different particle species being held at different locations. The particles to be fed out are selected by adjustment of the frequencies f1, f2 of the applied field or via the selected voltages U1, U2.

Figure 5:
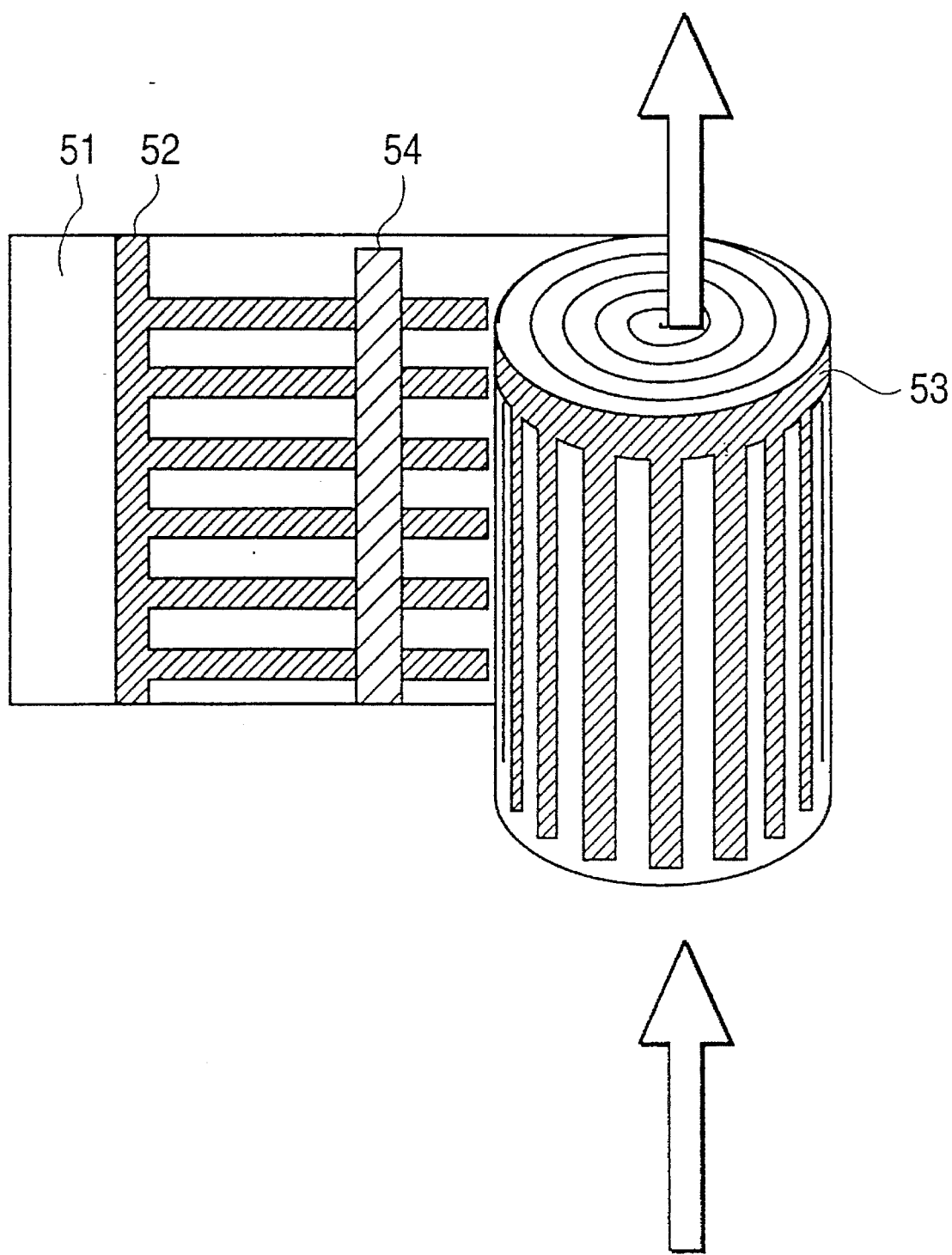
FIG. 5 illustrates a particle filter.

FIG. 5 illustrates a particle filter wrapped up to fore a reel whose end is unwrapped for the sake of clarity. Electrode systems 52, 53 are applied on both sides of an elongate sheet 51. Both the electrodes 52 on the first sheet surface, which extend in parallel with the longitudinal sheet extension, and the electrodes 53 on the other sheet surface, which extend in a direction normal to the longitudinal sheet extension, are conductively connected to each other at one end. Insulating bridges 54 are regularly spaced above the electrodes 52, which, following the wrapping of the sheet, prevent an electrical contact between the electrode systems and keep passage spaces free for the flow of the suspended mixture of particles. The flow of the corpuscular mixture through the reel is indicated by arrows. Dielectrophoretic holding fields serve to feed out certain species of particles from the corpuscular mixture flowing therethrough. The holding fields are generated by the application of a high-frequency alternating voltage between the electrode systems.

Figure 6:
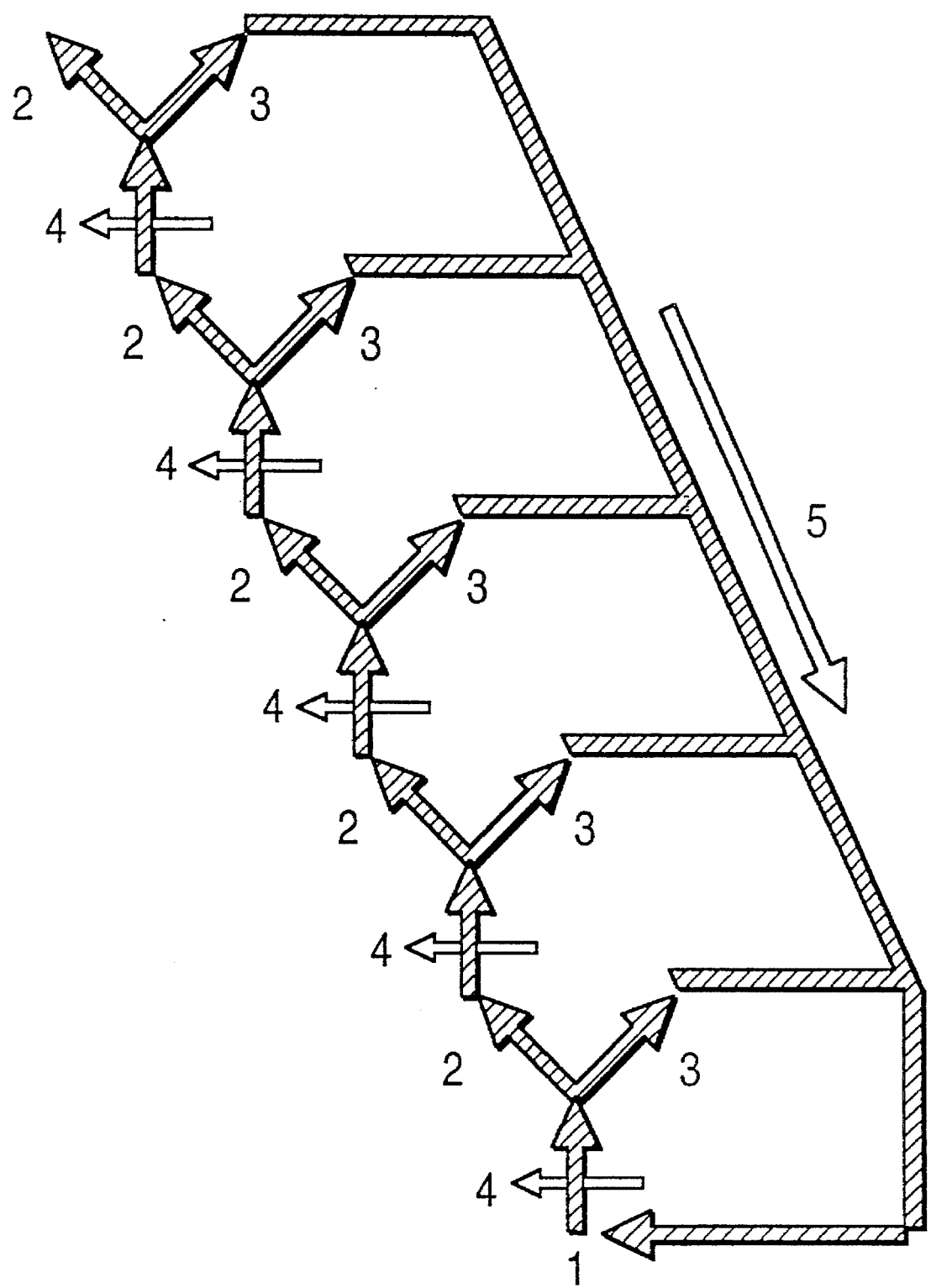
FIG. 6 shows a cascade arrangement.

FIG. 6 is an illustration of a cascade-shaped separating section. Five separating apparatuses (e.g. of the type illustrated in FIG. 2) are provided in tandem arrangement. The arrows 4 indicate that in this region the combination of dielectrophoresis and an additional force serves to split the corpuscular mixture 1 into two fractions 2, 3. The fraction of the particle species 2, which is fed out from the mixture, is passed through further separating stages for purification by elimination of remaining particles of the mixture. The corpuscular fraction 3 is recycled, for instance, through an electrical high-frequency travelling field 5 to the beginning of the cascade or a separating stage, respectively, in order to obtain the particles of species 2 which have remained in fraction 3. The cascade-shaped separating section is employed to achieve a particularly high grade of separation.

We claim:

1. Method of continuously separating mixtures of microscopic dielectric particles suspended in a liquid or a gel, comprising the steps of:

(a)(1) continuously forcing the particles to move on guide paths by applying electric high-frequency alternating fields as a guiding field, which present maxima and minima at microscopic spacings, and (a)(2) feeding certain particle species out from said guide path by applying at least one additional field of forces acting upon said particles and having a component orthogonal to said guide paths and with compensation of the forces enforcing the motion of said certain particle species on said guide paths; or (b)(1) forcing the particles onto guide paths by causing a suspension medium of the particles to flow in a presettable flow in a presettable direction, and (b)(2) feeding certain particle species out from said flow by applying at least one dielectrophoretic high-frequency field acting upon said particles, with compensation of the force acting upon said particles as a result of said flow.

2. Method according to claim 1, wherein step (a) includes utilizing an electric high-frequency field as guiding field, which travels in presettable directions.

3. Method according to claim 1 or 2, wherein step (a) includes generating said guiding field by a plurality of alternating fields which are different from each other in terms of frequency and phase.

4. Method according to any of claims 1 to 2, wherein the particle species to be fed out is selected by varying said additional field of forces or of said guiding field.

5. A method according to claim 1, wherein the step (a)(2) includes applying the at least one additional field of forces in the form of one of an electric field, a magnetic field, an optical field, a gravitational field, a field of flow and a corpuscular flux.

6. An apparatus for continuously separating mixtures of microscopic dielectric particles suspended in a liquid or gel, comprising:

(a)(1) means for continuously forcing the particles to move on guide paths including means for applying electric high-frequency alternating fields as a guiding field, which present maxima and minima at microscopic spacings, and (a)(2) means for feeding certain particles species out from the guide path by applying at least one additional field of forces acting upon the particles and having a component orthogonal to the guide paths and with compensation of the forces enforcing the motion of the certain particle species on the guide paths; or (b)(1) means for forcing the particles onto guide paths by causing a suspension medium of the particles to flow in a presettable direction, and (b)(2) means for feeding certain particle species out from the flow including means for applying at least one dielectrophoretic high-frequency field acting upon the particles with compensation of the force acting upon the particles as a result of the flow.

7. Apparatus according to claim 6, wherein two rows of electrodes are provided in parallel facing relationship, which enclose a linear or a curved flow channel.

8. Apparatus according to claim 6, wherein said electrodes generate said guiding field.

9. Apparatus according to claim 8, wherein two rows of electrodes are disposed in a chamber having an inflow and an outflow opening, which electrodes enclose a passage interconnecting said openings, and that on both sides, outside said passage, one additional electrode each is mounted along said rows of electrodes, with said additional electrodes being parallel with each other.

10. Apparatus according to claim 9, wherein a diaphragm is mounted at least between a row of electrodes and said additional electrode disposed along said row of electrodes, which diaphragm fills the cross-sectional space of said chamber.

11. Apparatus according to claim 8, wherein:

a row of electrodes elongate transversely with respect to the direction of said travelling field is disposed at regular spacings in parallel tandem relationship on a substrate in the direction of said travelling field, a first number of adjacent electrodes presents a central gap and forms a channel extending in the direction of said travelling field;

a second number of adjacent electrodes is configured to be continuous;

two isolating layers are mounted above said electrodes, which present a rectangular configuration in the region of said first number of adjacent electrodes, which largely cover said electrodes, enclose said channel formed by these electrodes, and which present a trapezoidal configuration in the region of said second number of electrodes such that the width of said channel enclosed by said layers increases in the direction of said travelling field;

a third elongate isolating layer is applied above said second number of electrodes in the center of said channel, which layer extends in the direction of said travelling field and bifurcates said channel into two channel branches in the region of its increasing width; and additional electrodes are applied on said first two isolating layers in the region of said first number of electrodes, and said additional electrodes extend in parallel relationship and in parallel with said channel they enclose.

12. Apparatus according to claim 6, wherein said electrodes are disposed along a passage where said suspension medium is flowing, said electrodes are connected to one or several high-frequency voltage sources for generating said additional field of forces, and said electrodes are configured so that said generated electric fields present inhomogeneities in the region of said passage and that said additional field of forces is generated which is effective in a direction orthogonal to said guiding field.

13. Apparatus according to claim 12, wherein said electrodes present surfaces having relief-like irregularities.

14. Apparatus according to claim 12, wherein said electrodes of each row are disposed in parallel relationship at different spacings along said flow direction, and that said electrodes of each row are connected to a high-frequency voltage source U1, U2 for electrically connecting two respectively adjacent electrodes to different poles of said voltage source.

15. Apparatus according to claim 12, wherein said electrodes form electrode systems provided for generating dielectrophoretic forces which are applied on both sides of a thin flexible material which is folded or wrapped to form a three-dimensional structure so as to produce passages enclosed by said electrode systems.

16. Apparatus according to claim 15, characterized in that a row of electrodes extending in the longitudinal extension of an elongate sheet is applied on one side of said sheet, said electrodes are interconnected at one end; insulating ribs are regularly spaced on said electrodes; on the other side of said sheet electrodes are applied which extend transversely with respect to the longitudinal extension of said sheet and which are conductively interconnected at one end; said sheet is wrapped in the longitudinal direction in such a way that said insulating ribs serve as spacers between the layers of said wrapped sheet; and a high-frequency alternating voltage is applied between said electrodes applied on both sides of said sheet.

17. Apparatus according claim 6, wherein the elements defining said particle orbits present traversable through holes or pores.

18. Apparatus according to any of claim 6, wherein surfaces of said electrodes present a relief-like surface structure of microscopic dimension so as to fore longitudinal channels in the direction of said corpuscular flux.

19. Apparatus according to any of claim 6, wherein surfaces of said electrodes are coated with insulating materials and that said coating presents troughs, corrugations or regions of different thicknesses.

20. Apparatus according to claim 6, wherein a base body carrying said electrodes is made of a semiconductor material, glass or ceramic, that said partial cavities, elevations or through holes are produced by etching processes, said electrodes are made of a chemically inert material, are structured by means of photolithographic methods and are galvanically moulded, and dielectric layers on said electrodes consist of $SiO_2$, $Si_3N_4$, barium titanate or $TiO_2$.

21. Apparatus according to claim 6, wherein a multi-electrode system for separating the particles, together with an electronic circuit for generating said fields and for analyzing the particle motions, is integrated on a common base body.

22. Apparatus according to any of claim 6, wherein a plurality of apparatuses is disposed in tandem in a cascade-type arrangement.

23. An apparatus according to claim 6, wherein the means for applying at least one additional field of forces provides the field in the form of one of an electric field, a magnetic field, an optical field, a gravitational field, a field of flow and a corpuscular flux.

* * * * *